(12) United States Patent
Imam et al.

(10) Patent No.: US 9,108,909 B1
(45) Date of Patent: Aug. 18, 2015

(54) CEREAL-BASED CHARCOAL BINDER

(75) Inventors: Syed H. Imam, Walnut Creek, CA (US);
Greg M. Glenn, American Canyon, CA (US); Bor-Sen Chiou, Walnut Creek, CA (US); William J. Orts, Burlingame, CA (US); Dustin Rains, Pleasanton, CA (US); Allison Fretwell, Pleasanton, CA (US); Greg Piche, Pleasanton, CA (US); Adam Slaboski, Pleasanton, CA (US); Stephen Fisher, Pleasanton, CA (US); Tomas Colussi, Pleasanton, CA (US); Don Swatling, Pleasanton, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 936 days.

(21) Appl. No.: 13/239,897

(22) Filed: Sep. 22, 2011

(51) Int. Cl.
| | |
|---|---|
| *C10L 5/00* | (2006.01) |
| *C07C 323/16* | (2006.01) |
| *C07C 323/25* | (2006.01) |
| *C07D 277/56* | (2006.01) |
| *C07D 213/32* | (2006.01) |
| *C07D 207/08* | (2006.01) |
| *C07D 211/60* | (2006.01) |
| *C07D 239/42* | (2006.01) |
| *C07D 309/38* | (2006.01) |
| *C07D 211/58* | (2006.01) |
| *C07D 317/28* | (2006.01) |
| *C07D 239/58* | (2006.01) |
| *C07D 317/22* | (2006.01) |
| *C07D 215/06* | (2006.01) |
| *C07D 233/64* | (2006.01) |
| *C07D 251/38* | (2006.01) |
| *C07D 319/06* | (2006.01) |

(52) U.S. Cl.
CPC ............ *C07C 323/16* (2013.01); *C07C 323/25* (2013.01); *C07D 207/08* (2013.01); *C07D 211/58* (2013.01); *C07D 211/60* (2013.01); *C07D 213/32* (2013.01); *C07D 215/06* (2013.01); *C07D 233/64* (2013.01); *C07D 239/42* (2013.01); *C07D 239/58* (2013.01); *C07D 251/38* (2013.01); *C07D 277/56* (2013.01); *C07D 309/38* (2013.01); *C07D 317/22* (2013.01); *C07D 317/28* (2013.01); *C07D 319/06* (2013.01)

(58) Field of Classification Search
CPC .. C07C 323/16; C07C 323/25; C07C 323/40; C07D 207/08; C07D 211/58; C07D 211/60; C07D 213/32; C07D 215/06; C07D 233/64; C07D 239/42; C07D 239/58; C07D 251/38; C07D 277/56; C07D 309/38; C07D 317/22; C07D 317/28; C07D 319/06; C07H 15/18; C07H 5/06
USPC .................................... 44/280, 544, 577, 554
See application file for complete search history.

(56) References Cited

U.S. PATENT DOCUMENTS

| 3,062,629 A * | 11/1962 | Margolin et al. ............... 44/577 |
| 5,009,671 A * | 4/1991 | Franke et al. .................... 44/598 |
| 2009/0119981 A1* | 5/2009 | Drozd et al. .................... 44/544 |
| 2011/0099887 A1* | 5/2011 | Stinson et al. .................. 44/280 |

* cited by examiner

*Primary Examiner* — James Goloboy
*Assistant Examiner* — Latosha Hines
(74) *Attorney, Agent, or Firm* — Robert D. Jones; John D. Fado; Lesley Shaw

(57) ABSTRACT

The cereal-based charcoal binder utilizes unrefined non-corn whole grains to replace the conventional cornstarch binder in solid charcoal fuels. The whole grain material is ground up, mixed with water, gelatinized, and then mixed with at least one dry ingredient to produce the solid charcoal fuel product.

8 Claims, No Drawings

CEREAL-BASED CHARCOAL BINDER

FIELD OF THE INVENTION

The present invention relates to a process for using cereal grains as binders. Specifically, the present invention relates to a method of using a non-corn cereal grain as a binder in a process for making a product, such as a charcoal briquette. The non-corn cereal grains include (at least) whole soft white wheat, oat, barely, sorghum and tapioca (cassava).

BACKGROUND OF THE INVENTION

Current manufacturers primarily use refined starch (such as cornstarch) as a binder in the charcoal manufacturing process. However, cornstarch has become increasingly expensive. Among other things, the use of corn-based products for sweeteners and energy products (e.g. ethanol) is creating an increased demand and corresponding higher prices To reduce manufacturing costs, charcoal product manufactures are exploring alternative binders and binder processes. Manufacturers have tried to eliminate some of the cornstarch binder by replacing the cornstarch with alternative binders such as clay and other similar materials. However, these alternative binders generally exhibit inadequate binding strength and the resulting modified charcoal products lack structural integrity. The modified products are unable to withstand the commercial manufacturing, packaging, and transportation processes.

The need exists for a charcoal binder that performs as effectively as the current cornstarch binder but has lower manufacturing costs. The current invention comprises an inexpensive, natural, non-corn binder that is equally as effective as the commercially available cornstarch binders. The inventors have found that (for example) an oat-based charcoal binder cost on average 40% less per pound than cornstarch. The current invention enables manufacturers to replace a high demand and high cost product with a (relatively) underutilized product, thereby decreasing manufacturing costs, broadening the base of the rural agricultural economy, and benefitting the American Farmer.

SUMMARY OF THE INVENTION

The current invention is directed to a solid fuel comprising a dry carbonaceous ingredient combined with an unrefined starch binder produced from processing a non-corn whole grain into a particle sizes ranging between 5-40 mesh. The solid fuel exhibits a dry strength of at least 50-150 lbf.

The current invention is also directed to a method for producing a solid fuel. The solid fuel is produced by processing a non-corn whole grain material and mixing the processed whole grain material with fluid to produce a slurry. The slurry is then gelatinized with the application of heat to form a gelatinized slurry. The gelatinized slurry is mixed with at least one carbonaceous dry ingredient to produce the solid fuel.

The current invention is further directed to a process for producing a whole grain-containing product. The whole grain product is produced by grinding a non-corn whole grain material and mixing the ground whole grain material with water to produce a slurry. The slurry is gelatinized with an application of heat of 170-200° F. to form a gelatinized slurry. The gelatinized slurry is mixed with at least one dry carbonaceous ingredient to produce the whole grain-containing product.

DETAILED DESCRIPTION OF PREFERRED EMBODIMENTS

Solid fuel briquettes are predominately comprised of two components: biomass char, which is relatively easy to ignite but combusts rapidly, and coal, which is more difficult to ignite and burns more slowly than biomass char, but which also burns at higher temperatures. The biomass char is combined with the coal, binders and other additives. The most common form of biomass char used in briquettes is wood char. Although specific embodiments discussed herein include wood char, it is intended that the invention encompasses all forms of biomass char including wood char.

"Wood Char" as used herein refers to the hard fibrous substance comprised of xylem that makes up the greater part of the stems, branches and roots of trees or shrubs beneath the bark and is found to a limited extent in herbaceous plants and which has been partially burned or scorched or otherwise converted to carbon. Wood char is a comprehensive term and includes retort chars, kiln chars, etc. Wood char as used herein can include bark.

"Coal" as used herein refers to a solid combustible substance formed by the partial decomposition of vegetable matter without free access of air and under the influence of moisture and often increased pressure and temperature that is widely used as a natural fuel. It is therefore understood that designations such as lignite, anthracite, semi-anthracite, bitumen, mineral carbons and mixtures of any of the foregoing, may singularly or collectively be referred to herein as coal.

"Other additives" as used herein refers to components which may be desirably included in a briquette formulation to enhance appearance or aesthetic use qualities thereof. Examples include, but are not limited to builders, fillers, density modifiers, ash whiteness enhancers, release agents, ignition aids, sawdust, burn enhancers, and solvents, etc.

One known process of making a solid fuel briquette involves preparing a starch slurry, which typically contains approximately 77% water, 20% refined starch (e.g., cornstarch) and 3% of other additives. Next the slurry is gelatinized by heating the suspended starch solution, for example in a steam injection cooker, and brought to a temperature between 160° F. to 210° F. The hot slurry is then mixed with the other components and finally the mixture is formed into the desired shape by rolling, extruding, pressing, etc.

The briquettes are then dried in large tunnel dryers where they are piled on perforated wire belts and hot air is blown through the belts to dry off excess moisture that was added in the starch slurry. This step hardens the starch binder so that the briquettes achieve a higher strength to enable them to be handled, packaged and shipped. The briquettes are then packaged in standard bag filling equipment. Other non-limiting methods of making briquettes are described in U.S. Pat. No. 5,762,656 to Burke and U.S. Pat. No. 5,049,333, which are herein incorporated by reference in their entirety.

In accordance with the current invention, the inventors have found a new process for making briquettes using non-corn cereal grains, such as whole soft white wheat, oat, barley, tapioca (i.e. cassava), and sorghum (and combinations thereof) rather than a refined starch material. Based on their observations, the inventors theorize that the presence of soluble fiber enables the grains to act as an effective binder.

Accordingly, the current invention does not require the use of a refined cornstarch. As indicated in Table 1 (below), briquettes made by the new process surprisingly have parity or better green and dry strength relative to briquettes made with refined starch.

TABLE 1

| Binder | Wet Strength (Kg)* | Dry Strength (Kg)* |
|---|---|---|
| Cornstarch Binder (Control) | 16.0 | 26.0 |
| Cereals: Oat | 28.9 | 52.0 |
| Barley | 26.7 | 53.0 |
| Soft White Wheat | 26.2 | 51.8 |

*Average of 4 samples tested.

"Whole grain" as used herein refers to the whole starch-containing portion of a cereal grain material such as wheat, barley, oat, etc. The whole grain contains four basic components: starch, germ, fiber and protein.

"Refined starch" as used herein refers to starch that has been extracted from a whole kernel material by any process known in the art. An example of a refined starch is cornstarch.

"Green strength" (or alternatively, "Wet Strength") as used herein refers to the strength of a briquette immediately upon formation and prior to heating in (for example) a reducing furnace. High green strength is important to minimize flaking or crumbling of briquettes in subsequent processing and handling. The green strength is measured by compressing the briquette and measuring the maximum pressure required to break the briquette. As indicated by the data in Table 1, briquettes made by the process of the current invention have superior wet strength relative to conventional cornstarch-binder briquettes (i.e. the Control).

"Dry strength" as used herein refers to the strength of the briquette after heating and wherein the moisture content is about 5% or less. Dry strength is measured by compressing the briquette and measuring the maximum pressure required to break the briquette. As indicated by the data in Table 1, briquettes made by the process of the current invention have superior dry strength relative to conventional cornstarch-binder briquettes (i.e. the Control). Oat-based (for example) briquettes can be manufactured at a significantly lower cost than briquettes made by a process using a refined starch material, such as cornstarch.

In the preferred embodiment, the process of making a solid fuel briquette, involves milling (for example) oats into a fine powder using a 1/16" grate in a hammer mill to produce oat powder that has mean particulate size of approximately 30 mesh. The milled oats are mixed with water and cooked to produce a thick slurry. The process and resulting slurry is very similar to the cornstarch slurry-forming process described above. The milled oats replace cornstarch in the normal slurry pre-blend that comprises the binder, water, and nitrate.

The pre-blend is then mixed at 140° F. and cooked at a target temperature of 180° F. before it is added to the dry mixture of char, lignite, sawdust, and limestone. The combination of these two mixtures is the pressed into the final briquettes. A high green moisture target of approximately 30% provides suitable green strength performance of the pressed briquettes. The briquette may then be dried to evaporate excess moisture added in the starch slurry.

The inventors have found that a slightly higher ratio of oats to conventional briquette ingredients is required to deliver equivalent briquette strength relative to the ratio of cornstarch currently required. However, there is no need to add modifying agents (as is the case with cornstarch) to the oat slurry to initiate binding. The only requirement for the oats to be effective is to mill them into a fine powder. Once mixed with water, the cooking process is much simpler than the process used in conjunction with cellulose-based binding materials. For example, the cooking process occurs at a lower temperature and does not require any added pressure.

A blind test was conducted to see if test subjects could discern any apparent differences in the smells, appearance, and smoke produced by the powdered oat briquettes relative to conventional briquettes. After exposure to the oat-binder briquettes, none of the test subjects indicated that there was any noticeable difference between the smell of the oat-binder briquettes and the control cornstarch-binder briquettes. Test subjects also could not distinguish between any difference in the volume of smoke produced by the respective briquettes.

In alternative embodiments, varying amounts of whole grains may be used in the starch slurry, described supra. In one embodiment, the ground whole grain is present in an amount of from about 10% to about 40% by weight of the slurry. In another embodiment, the ground whole grain is present in an amount of from about 20% to about 30% by weight of the slurry. In a third embodiment, the ground whole grain is present in an amount of from about 20% to about 25% by weight of the slurry.

In one alternative embodiment, the water is present in a weight percent amount of about 50% to about 80% of the slurry. In another embodiment, the water is present in a weight percent amount of about 60% to about 75% of the slurry. In a third embodiment, the water is present in a weight percent amount of about 70% to about 80% of the slurry.

In one further alternative embodiments, the whole grain is ground to a size of about 5 mesh to about 40 mesh. The whole grain can be ground or otherwise processed using any process known in the art so that the desired particle size is achieved.

In an additional embodiment, the product is a solid fuel briquette and the green strength is about 5 lbf to about 30 lbf. In another embodiment, the green strength is about 10 lbf to about 20 lbf. In a third embodiment, the green strength is about 5 lbf to about 15 lbf. In another embodiment, the dry strength of the briquette is 25 lbf to about 150 lbf. In yet another embodiment, the dry strength of the briquette is 80 lbf to about 125 lbf. In another embodiment, the dry strength of the briquettette is about 30 lbf to about 75 lbf.

In a further alternative embodiment, the binder product of the current invention is used any desired output product that is made by the present inventive manufacturing process and does not contain refined starch. Non-limiting examples of products which can be made by the inventive process described herein include solid fuel briquettes, cat litter, nonwoven materials, tortilla chips, and other foodstuffs.

EXAMPLE

The compositions and data used in this example describe specific embodiments of the compositions of the present invention, but are not intended to be limiting thereof. Other modifications can be undertaken by the skilled artisan without departing from the spirit and scope of this invention. For example, the briquettes in the examples are formed into pillow shapes, but the invention is suitable for other briquette shapes as well.

All exemplified compositions can be prepared by conventional formulation and mixing techniques. Component amounts are listed as amounts listed in percentage ("%'s") are in weight percent of the composition alone and exclude minor materials such as fillers, etc., typically used to modify the compositions characteristics.

In this example, a briquette (Charcoal Briquette A) comprised of 10% milled oats was formed by first preparing a slurry of milled oats by mixing about 25% ground 30 mesh size oats, about 2.3% burn enhancer and about 72.7% water. The slurry was mixed for about 5 minutes at 140° F. and then gelatinized by cooking at a temperature of about 180° F. The hot gelatinized slurry was then mixed with carbonaceous components, which includes at least wood char. The Green Moisture target was 30%. Finally, the mixture was formed into a pillow shape by a press process. Accordingly, no cornstarch was used in the process of making Charcoal Briquette A.

Another briquette (Charcoal Briquette B) comprised of 8.5% cornstarch was formed by first preparing a slurry of ground corn by mixing about 20% cornstarch, 2% burn enhancer, and about 77% water. The slurry was mixed for about 5 minutes at 140° F. and then gelatinized by cooking at a temperature of about 180° F. The hot gelatinized slurry was then mixed with carbonaceous components, which includes at least wood char. Finally, the mixture was formed into a pillow shape by a press process.

The green strength of the samples Charcoal Briquettes A and B were tested according to the following method: The shaped briquettes were centered under a cylindrical probe in a Texture Analyzer (Texture Technologies Corp., Scarsdale, N.Y.). The cylindrical probe was then pressed down into the briquettete using the following parameters:
Test Speed: 2.5 mm/s
Rupture Test Distance: 1.0 mm
Cylindrical Probe Dimensions:
  Height: 1⅜"
  Diameter: 0.5"

Briquette Sample A and Sample B of Example 1 were then dried at about 120° C. for about 6 hours until the moisture content was about 5%. They were then cooled to room temperature and equilibrated for at least 24 hrs prior to testing. The dry strength of each was then tested according to the following method: The shaped briquettes were centered under a conical probe in a Texture Analyzer (Texture Technologies Corp., Scarsdale, N.Y.). The point of the conical probe was placed over the briquettete and pressed into the briquette using the following parameters:
Test Speed: 2.5 mm/s
Rupture Test Distance: 1.0 mm
Conical Probe Dimensions:
  Height: ⅞"
  Diameter: 0.5"

Briquettes were measured to obtain the average green strength, dry strength and density. The results of the test are presented in Table 2 below and show that briquettes made by the process of the current invention are stronger than briquettes made using corn starch.

TABLE 2

| Green Stength (lbf) | | Dry Strength (lbf) | | Density (g/cm³) | |
|---|---|---|---|---|---|
| Briquette A | Briquette B | Briquette A | Briquette B | Briquette A | Briquette B |
| 14 | 13 | 63 | 38 | 0.7 | 0.66 |

Briquettes were also tested to obtain data regarding product burn characteristics. Specifically, the briquettes were tested to determine Charcoal Briquette A was made with milled oats, and Charcoal Briquette B was made with conventional cornstarch.

The results of the test are presented below in Table 3. The Table 3 data is the average of two batches. The average burn data for Briquette A and Briquette B were measured. The tested characteristics included Ease of Ignition as exhibited by a percentage of Visible Ash (VA) at 10 minutes, and Burn Time as exhibited by the amount of time (minutes) that the briquettes burned at over 380° F., which is a measure of the cooking time a typical user of the briquettes will have. Preferably, the VA at 10 minutes is greater than 25% and the burn time over 380° F. is greater than 30 minutes.

The results of the burn tests show that the oat-binder charcoal briquettes of the current invention exhibited performance that was at least equivalent to conventional cornstarch briquettes, and in fact exceeded the conventional briquettes in Ease of Ignition and Burn time tests.

TABLE 3

| Ease of Ignition (VA %) | | Burn Time (min) | |
|---|---|---|---|
| Briquette A | Briquette B | Briquette A | Briquette B |
| 46 | 51 | 41 | 46 |

For the foregoing reasons, it is clear that the invention provides an innovative innovative alternative to cornstarch-binder briquettes. Although the only example shown here involves the use of an oat-based binder, the inventors have also confirmed that similar processes work for other non-corn cereal grains such as whole soft white wheat, oat, barely, sorghum, and tapioca (cassava).

The invention may be modified in multiple ways and applied in various technological applications. The current invention may be modified and customized as required by a specific operation or application, and the individual components may be modified and defined, as required, to achieve the desired result. Although some of the materials of used in the process and/or formulation are not described, they may include a variety of compositions consistent with the function of the invention. Such variations are not to be regarded as a departure from the spirit and scope of the invention, and all such modifications as would be obvious to one skilled in the art are intended to be included within the scope of the following claims.

We claim:

1. A solid fuel comprising:
  a dry carbonaceous ingredient;
  an unrefined starch binder produced from processing a non-corn whole grain into a particle sizes ranging between 5-40 mesh;
  wherein the dry carbonaceous ingredient is combined with the unrefined starch binder so that the solid fuel has a dry strength of at least 50-150 lbf.

2. The solid fuel of claim 1 wherein the solid fuel has a green strength of 5-30 lbf.

3. The solid fuel of claim 1 wherein the unrefined starch is processed from one of whole soft white wheat, oat, barely, sorghum and tapioca (cassava), or a combination thereof.

4. The solid fuel of claim 1 wherein the whole grain is processed by grinding.

5. The solid fuel of claim 1 wherein the dry carbonaceous ingredient is selected from the group consisting of biomass char, coal and combinations thereof.

6. The solid fuel of claim 1 wherein the solid fuel exhibits a visible ash at 10 minutes that is greater than 25%.

7. The solid fuel of claim 1 wherein the burn time at over 380° F. is greater than 30 minutes.

8. The solid fuel of claim 1 wherein the solid fuel comprises a charcoal briquette.

* * * * *